(12) United States Patent
Lee et al.

(10) Patent No.: US 10,478,384 B2
(45) Date of Patent: Nov. 19, 2019

(54) DENTAL COMPOSITION

(71) Applicant: Zimmer Dental, Inc., Carlsbad, CA (US)

(72) Inventors: Jin Whan Lee, Naperville, IL (US); Hai Bo Wen, Carlsbad, CA (US); Jeffrey Bassett, Vista, CA (US); Mike Warner, Carlsbad, CA (US)

(73) Assignee: Zimmer Dental, Inc., Carlsbad, CA (US)

( * ) Notice: Subject to any disclaimer, the term of this patent is extended or adjusted under 35 U.S.C. 154(b) by 690 days.

(21) Appl. No.: 14/101,936

(22) Filed: Dec. 10, 2013

(65) Prior Publication Data

US 2014/0161901 A1    Jun. 12, 2014

Related U.S. Application Data (60) Provisional application No. 61/735,671, filed on Dec. 11, 2012, provisional application No. 61/888,683, filed on Oct. 9, 2013.

(51) Int. Cl.
| | | |
|---|---|---|
| *A61K 6/02* | (2006.01) | |
| *A61K 6/033* | (2006.01) | |
| *A61Q 11/00* | (2006.01) | |
| *A61K 6/00* | (2006.01) | |

(52) U.S. Cl.
CPC .......... *A61K 6/0044* (2013.01); *A61K 6/0041* (2013.01)

(58) Field of Classification Search
None
See application file for complete search history.

(56) References Cited

U.S. PATENT DOCUMENTS

| | | | | |
|---|---|---|---|---|
| 5,091,441 | A * | 2/1992 | Omura | A61K 6/0023 220/903 |
| 6,787,584 | B2 * | 9/2004 | Jia | A61K 6/0032 106/35 |
| 7,204,875 | B2 * | 4/2007 | Jia | A61K 6/0023 106/35 |
| 2002/0045678 | A1 * | 4/2002 | Lopez | A61K 6/0017 523/116 |
| 2007/0098799 | A1 * | 5/2007 | Zhang | A61L 27/46 424/486 |

OTHER PUBLICATIONS

Roberts et al. (Dental Materials 2008, 24, 149-164).*

* cited by examiner

*Primary Examiner* — Abigail Vanhorn
(74) *Attorney, Agent, or Firm* — Schwegman Lundberg & Woessner, P.A.

(57) ABSTRACT

Dental compositions are disclosed. A dental composition can include a reaction produce of a reaction mixture comprising a first mixture and a second mixture. The first mixture can include a ceramic based biomaterial, and the second mixture can include mineral trioxide aggregate and a phosphoric acid monomer.

20 Claims, 2 Drawing Sheets

DENTAL COMPOSITION

CLAIM OF PRIORITY

This application claims the benefit of U.S. Provisional Patent Application Ser. No. 61/735,671, filed on Dec. 11, 2012 and U.S. Provisional Patent Application 61/888,683 filed on Oct. 9, 2013, the benefit of priority of which is claimed hereby, and which is incorporated by reference herein in its entirety.

TECHNICAL FIELD

The present patent document pertains generally to dental compositions for use with dental implants. More particularly, but not by way of limitation, the patent document pertains to a two-part dental composition. The disclosure can also be applied to other orthopedic applications such as spinal pedicel screws, bone screws used in trauma applications or other bone screws.

BACKGROUND

A dental implant can be used in an oral treatment procedure to restore appearance or function of a removed tooth. A dental implant can mimic a root of a natural tooth that is replaced. A surgeon can replace the natural tooth with a prosthetic tooth that is mounted on a coronal portion of an abutment, which in turn, is attached to the dental implant on an apical portion. During surgery, the surgeon can insert the dental implant into a dental bone cavity. A successful dental implant procedure generally requires more than bone affixation or osseointegration.

Implant success can also require maintenance of the cortical bone at the coronal crest of the implant and maintenance of soft tissue structures in the implant region. The health of tissues in this region contributes to the aesthetic appearance of a full restoration. Maintenance of healthy tissue in the implant region can also lead to the creation of a tissue seal that hinders the propagation of infection along the implant body.

OVERVIEW

The present disclosure can include a dental composition for use with a dental implant. The dental composition can include a ceramic based biomaterial (e.g., hydroxyapatite (HA)), mineral trioxide aggregate (MTA), and a phosphoric acid monomer. The dental composition is a two-part self-curable adhesive that can be used with dental implants. The disclosure seeks to offer the benefit of providing a dental composition that can be applied to a dental implant, where the dental composition is biocompatible, improves healing time, and improves bonding of the dental implant to the surrounding tissues. The dental composition of the present disclosure can increase the rate of bone apposition and increase primary stability.

Previous approaches have incorporated HA coatings onto dental implants, however, amorphous or semi-crystallized HA can degrade over time into amorphous calcium phosphates. The amorphous calcium phosphates can be soluble in aqueous and physiological solutions and reduce the adhesive and cohesive strength of the HA coating and increase the delamination and dissolution rate. The increased delamination and dissolution rate can result in premature failure of the dental implant. Dental implants can be formed from titanium or titanium alloys, and while a non-coated dental implant can provide mechanical strength, non-coated dental implants remain bioinert and may have reduced bonding to the surrounding tissues.

The present disclosure incorporates a ceramic based biomaterial (e.g., HA) into a dental composition with MTA and 10-methacryloyloxydecl dihydrogen phosphate (MDP). The MTA can have sealing capability and can release calcium ions when in contact with physiological solutions. The MTA can be a scaffold, which can be suitable for bone-tissue engineering applications. Providing a dental composition with the MTA and the ceramic based biomaterial (e.g., HA) can promote bone formation. The phosphoric acid monomer can have the ability to bond with calcium ions and the ceramic based biomaterial, as well as the surrounding bone and tissue. The phosphoric acid monomer can bond with the dental implant, which can reduce the risk of delamination. The dental composition of the present disclosure can increase the bonding to the surrounding tissue and bone and to the dental implant, which can reduce the risk of delamination. The dental composition of the present disclosure can reduce crestal bone resorption, and promote new bone formation, which can lead to maximum bone contact with the implant.

This Overview is intended to provide an overview of subject matter of the present patent document. It is not intended to provide an exclusive or exhaustive explanation of the invention. The detailed description is included to provide further information about the present patent document.

To further describe the compositions, methods, and systems disclosed herein, a non-limiting list of examples is provided here:

In Example 1, a dental composition comprises a reaction product of a reaction mixture. The reaction mixture can include a first mixture and a second mixture. The first mixture can include a ceramic based biomaterial, and the second mixture can include mineral trioxide aggregate and a phosphoric acid monomer.

In Example 2, the subject matter of Example 1 can optionally be configured such that the ceramic based biomaterial is chosen from calcium phosphates, strontium phosphates, calcium carbonates, calcium sulfate, and calcium hydroxide.

In Example 3, the subject matter of any one or any combination of Examples 1 or 2 can optionally be configured such that about 50 weight percent to about 80 weight percent of the first mixture comprises the ceramic based biomaterial, the weight percent based on a total weight of the first mixture.

In Example 4, the subject matter of any one or any combination of Examples 1 through 3 can optionally be configured such that about 60 weight percent of the first mixture comprises the ceramic based biomaterial, the weight percent based on a total weight of the first mixture.

In Example 5, the subject matter of any one or any combination of Examples 1 through 4 can optionally be configured such that about 5 weight percent to about 50 weight percent of the second mixture comprises the mineral trioxide aggregate, the weight percent based on a total weight of the second mixture.

In Example 6, the subject matter of any one or any combination of Examples 1 through 5 can optionally be configured such that the phosphoric acid monomer is chosen from at least one of 1-methacryloyloxydecane-10-phosphate, 1-methacryloyloxyhexane-6-phosphate, 1-methacryloylaminodecane-10-phosphate, 1-acryloylaminohexane-6- phosphate, 1,3-dimethacryloyloxypropane-2-phosphate, and 1,3-dimethacryloylaminopropane-2-phosphate.

In Example 7, the subject matter of any one or any combination of Examples 1 through 6 can optionally be configured such that about 1 weight percent to about 15 weight percent of the second mixture comprises the phosphoric acid monomer, the weight percent based on a total weight of the second mixture.

In Example 8, the subject matter of any one or any combination of Examples 1 through 7 can optionally be configured such that about 15 weight percent to about 55 weight percent of the first mixture comprises a diluent, the weight percent based on a total weight of the first mixture.

In Example 9, the subject matter of any one or any combination of Examples 1 through 8 can optionally be configured such that about 2 weight percent to about 8 weight percent of the first mixture comprises N,N-di(2-hydroxyethyl)p-toluidine, the weight percent based on a total weight of the first mixture.

In Example 10, the subject matter of any one or any combination of Examples 1 through 9 can optionally be configured such that about 10 weight percent to about 50 weight percent of the second mixture comprises a bioactive glass, the weight percent based on a total weight of the second mixture.

In Example 11, the subject matter of any one or any combination of Examples 1 through 10 can optionally be configured such that about 0.5 weight percent to about 6 weight percent of the second mixture comprises a peroxide, the weight percent based on a total weight of the second mixture.

In Example 12, the subject matter of any one or any combination of Examples 1 through 11 can optionally be configured such that the first mixture includes 60 weight percent of hydroxyapatite, 35 weight percent of a diluent, and 5 weight percent of N,N-di(2-hydroxyethyl)p-toluidine the weight percent based on a total weight of the first mixture.

In Example 13, the subject matter of any one or any combination of Examples 1 through 12 can optionally be configured such that the diluent is tetra-ethylene glycol dimethacrylate.

In Example 14, the subject matter of any one or any combination of Examples 1 through 13 can optionally be configured such that the second mixture includes 25 weight percent of the mineral trioxide aggregate, 5 weight percent of the phosphoric acid monomer, 37 weight percent of a diluent, 3 weight percent of a peroxide, and 30 weight percent of a bioactive glass, the weight percent based on a total weight of the second mixture.

In Example 15, the subject matter of any one or any combination of Examples 1 through 14 can optionally be configured such that the diluent is 1-methacryloyloxydecane-10-phosphate, the peroxide is benzoyl peroxide, and the bioactive glass has a composition including a formulation including 46.1 mole percent of silicon dioxide, 2.6 mole percent of phosphorus pentoxide, 26.9 mole percent of calcium oxide, and 24.4 mole percent of sodium oxide.

In Example 16, a method can include obtaining or providing a first mixture including a ceramic based biomaterial and obtaining or providing a second mixture including mineral trioxide aggregate and a phosphoric acid monomer.

In Example 17, the subject matter of any one or any combination of Examples 1 through 16 can optionally be configured such that obtaining or providing the first mixture can include combining the ceramic based biomaterial with a diluent and N,N-di(2-hydroxyethyl)p-toluidine.

In Example 18, the subject matter of any one or any combination of Examples 1 through 15 can optionally be configured such that obtaining or providing the first mixture can include dissolving the N,N-di(2-hydroxyethyl)p-toluidine in the diluent to form a first solution, and mixing the first solution with the ceramic based biomaterial to form the first mixture.

In Example 19, the subject matter of any one or any combination of Examples 1 through 18 can optionally be configured such that obtaining or providing the second mixture can include combining the mineral trioxide aggregate and the phosphoric acid monomer with a diluent, a bioactive glass, and a peroxide.

In Example 20, the subject matter of any one or any combination of Examples 1 through 19 can optionally be configured such that obtaining or providing the second mixture can include dissolving the phosphoric acid monomer and the peroxide in the diluent to form a second solution, and mixing the second solution with the mineral trioxide aggregate and the bioactive glass to form the second mixture.

In Example 21, the subject matter of any one or any combination of Examples 1 through 20 can optionally be configured such that the first mixture can include 50 weight percent to 90 weight percent of hydroxyapatite, 15 weight percent to 55 weight percent of a diluent, and 2 weight percent to 8 weight percent of N,N-di(2-hydroxyethyl)p-toluidine, the weight percent based on a total weight of the first mixture.

In Example 22, the subject matter of any one or any combination of Examples 1 through 21 can optionally be configured such that the second mixture can include 5 weight percent to 50 weight percent of mineral trioxide aggregate, 1 weight percent to 15 weight percent of the phosphoric acid monomer, 15 weight percent to 57 weight percent of a diluent, 10 weight percent to 50 weight percent of a bioactive glass, and 0.5 weight percent to 6.0 weight percent of a peroxide, the weight percent based on a total weight of the second mixture.

In Example 23, the subject matter of any one or any combination of Examples 1 through 22 can optionally be configured to include combining the first mixture and the second mixture to form a dental composition or a component thereof.

In Example 24, the subject matter of any one or any combination of Examples 1 through 23 can optionally be configured to such that combining the first mixture and the second mixture to form a dental composition can include activating a dual syringe assembly having a first syringe including the first mixture, a second syringe including the second mixture, and a mixing tip, wherein the dual syringe assembly provides a homogeneous mixture upon dispensing the dental composition from an exit opening of the mixing tip.

In Example 25, the subject matter of any one or any combination of Examples 1 through 24 can optionally include applying the dental composition to a dental implant.

In Example 26, the subject matter of any one or any combination of Examples 1 through 25 can optionally be configured such that applying the dental composition to the dental implant includes coating a portion of an exterior surface of the dental implant, wherein the portion is configured to be inserted into an implant site within a patient.

In Example 27, a system can include a dental implant having a body portion configured to be inserted into a dental cavity of a patient, and a dental composition configured to be applied to at least the body portion. The dental composition including a reaction product of a reaction mixture comprising a first mixture comprising a ceramic based biomaterial, and a second mixture comprising mineral trioxide aggregate and a phosphoric acid monomer.

In Example 28, the subject matter of any one or any combination of Examples 1 through 27 can optionally be configured such that the dental implant is a non-threaded cylinder.

In Example 29, the subject matter of any one or any combination of Examples 1 through 27 can optionally be configured such that at least a portion of the body portion includes a porous material.

In Example 29, the subject matter of any one or any combination of Examples 1 through 27 can optionally be configured such that a surface of the dental implant has a ceramic based biomaterial applied to at least the body portion.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

It can be desirable to increase an initial stability of a dental implant within the surrounding tissue. The present dental coating composition (also referred to as "coating composition" and "composition") and methods provide for a biocompatible coating that can increase healing and increase the initial stability of a dental implant within a dental bone cavity by having an increased bond to the metal implant and surrounding tissues as compared to other coatings or dental implants with no coatings. The coating composition of the present disclosure includes a ceramic based biomaterial (e.g., hydroxyapatite (HA)), mineral trioxide aggregate (MTA), and 10-methacryloyloxydecyl dihydrogen phosphate (MDP). In an example, the coating composition can be obtained by reacting a first mixture including the ceramic based biomaterial with a second mixture including the MTA and MDP.

In an example, the ceramic based biomaterial can be chosen from calcium phosphates, strontium phosphates, calcium carbonates, calcium sulfate, and calcium hydroxide. In an example, the ceramic based biomaterial is hydroxyapatite (HA), also referred to as hydroxylapatite, that is a naturally occurring mineral form of calcium apatite having the chemical formula $Ca_5(PO_4)_3(OH)$. The ceramic based biomaterial can be added to a first mixture of the coating composition prior to mixing with the second mixture including the MDP and MTA. The ceramic based biomaterial can affect the osseointegration mechanism due to the oseoconductive property of the ceramic based biomaterial. That is, the ceramic based biomaterial can release calcium ions into surrounding tissue.

The first mixture can include the ceramic based biomaterial within a range of about 50 weight percent (wt. %) to about 80 wt. %, the weight percent based on a total weight of the first mixture. For example, the first mixture can include 55 wt. %, 60 wt. %, 65 wt. %, 70 wt. %, and 75 wt. % of the ceramic based biomaterial. In one example, the first mixture comprises 60 wt. % of HA.

The first mixture can also include a diluent. The diluent can be a cross-linking agent that can react with one or more initiators, such as initiators discussed herein. In an example, the diluent can be chosen from dimethacrylates, including mono-, di-, tri-, or tetra-ethylene glycol dimethacrylate; alkyl methacrylates, including 2-hydroxyethyl methacrylate and 2-hydroxypropyl methacrylate; ethylene glycol methacrylates, including ethylene glycol methacrylate, diethylene glycol methacrylate, tri(ethylene glycol)dimethacrylate and tetra(ethylene glycol)dimethacrylate; and diol dimethacrylates including 1,4-butanedioldimethacrylate, dodecanedioldimethacrylate, and 1,6-hexanedioldimethacrylate (HDDMA). In one example, the diluent can be tetra-ethylene glycol dimethacrylate (TEGDMA). In an example, the first mixture can include the diluent within a range of about 15 wt. % to about 55 wt. %, the weight percent based on the total weight of the first mixture.

For example, the first mixture can include 20 wt. %, 25 wt. %, 30 wt. %, 35 wt. %, 40 wt. %, 45 wt. %, and 50 wt. % of the diluent. In one example, the first mixture comprises 35 wt. % of the cross-linking agent.

The first mixture can also include an initiator such as N,N-di(2-hydroxyethyl)p-toluidine (DEPT). In an example, the first mixture comprises the DEPT within a range of from 2 wt. % to 8 wt. %, the weight percent based on a total weight of the first mixture. For example, the first mixture can include 3 wt. %, 4 wt. %, 5 wt. %, 6 wt. %, and 8 wt. % of DEPT. In one example, the first mixture comprises 5 wt. % of the DEPT.

As discussed herein, the dental composition can be formed by reacting the first mixture with the second mixture. The second mixture can include a phosphoric acid ester monomer and mineral trioxide aggregate.

The phosphoric acid ester monomer can be a dental adhesive monomer that can chemically bond to native bone tissue encountered. The phosphoric acid ester monomer can have the general formula $O=P(OR^3)_m(OR^4)_{3-m}$ and has at least one residue $R^3$ which contains one or two polymerizable groups, e.g., aklenylene groups. In some examples, $R^3$ can be a $(C_2-C_{20})$hydrocarbyl optionally interrupted by 0, 1, 2, or 3 oxygen atoms, optionally substituted by O=(oxo), and including at least one aliphatic unsaturated carbon-carbon bond. The phosphoric acid monomer can be a methacryloyloxy$(C_1-C_{20})$alkylphosphate. The phosphoric acid monomer can be an acryloylamino$(C_1-C_{20})$alkylphosphate. The phosphoric acid monomer can be a dimethacryloylamino$(C_1-C_{20})$alkylphosphate. Examples of the phosphoric acid ester monomer can include:

1-methacryloyloxydecane-10-phosphate (MDP)

1-methacryloyloxyhexane-6-phosphate (MHP)

1-methacryloylaminodecane-10-phosphate (MADP)

1-acryloylaminohexane-6-phosphate (AAHP)

1,3-dimethacryloyloxypropane-2-phosphate (DMPP)

and 1,3-dimethacryloylaminopropane-2-phosphate (DMAPP)

In one example, the phosphoric acid ester monomer is MDP. In an example, the second mixture includes the phosphoric acid ester monomer within a range of about 1 wt. % to about 15 wt. %, the weight percent based on a total weight of the second mixture. For example, the second mixture can include the phosphor acid ester monomer within a range of about 2 wt. % to about 14 wt. % such as 4 wt. %, 6 wt. %, 8 wt. %, 10 wt. %, and 12 wt. %, the weight percent based on the total weight of the second mixture. In one example, the second mixture includes 5 wt. % of the phosphoric acid ester monomer, the weight percent based on the total weight of the second mixture.

In an example, the second mixture includes mineral trioxide aggregate (MTA). MTA is a mixture of refined Portland cement and bismuth oxide consisting of $(CaO)_3.SiO_2$, $(CaO)_2.SiO_2$, $(CaO)_3.Al_2O_3$, $(CaO)_4.Al_2O_3.Fe_2O_3$, $CaSO_4.2H_2O$, and $Bi_2O_3$. When the MTA reacts with surrounding moisture, the MTA can have a self-setting mechanism and can solidify less than 3 hours. The MTA can release calcium ions that can contact neighboring tissue and bone to provide for bone fixation. The second mixture can include greater than 10 wt. % of the MTA, the weight percent based on the total weight of the second mixture. The second mixture can include the MTA within a range of about 5 wt. % to about 50 wt. %, the weight percent based on the total weight of the second mixture. For example, the second mixture can include the MTA within a range of about 10 wt. % to about 45 wt. %, such as 15 wt. %, 20 wt. %, 25 wt. %, 30 wt. %, 35 wt. %, and 40 wt. %. In one example, the second mixture includes 25 wt. % of the MTA.

In an example, the second mixture can include a bioactive glass. The bioactive glass is biocompatible and can act as a sealer interlocked within the composite and bond with native bone. The bioactive glass can also act to provide antibacterial properties, enhance osteoblast activity and angiogenesis, while inhibiting osteoclastic activity. The bioactive glass can be chosen from conventional silicate bioactive glass, borate-based glasses, and phosphate-based glasses. In an example, the bioactive glass can have a formulation including at least one of: 1) 30-60 mole percent of silicon dioxide, 10-50 mole percent of calcium oxide, and 5-40 mole percent of sodium oxide, 2) 46.1 mole percent of silicon dioxide, 2.6 mole percent of phosphorus pentoxide, 26.9 mole percent of calcium oxide, and 24.4 mole percent of sodium oxide, and 3) 53 mole percent of silicon dioxide, 4 mole percent of phosphorus pentoxide 20 mole percent of calcium oxide, and 23 mole percent of sodium oxide The second mixture can include the bioactive glass within a range of about 10 wt. % to about 50 wt. %, the weight percent based on the total weight of the second mixture. For example, the second mixture can include the bioactive glass within a range of about 15 wt. % to about 45 wt. %, such as 20 wt. %, 25 wt. %, 30 wt. %, 35 wt. %, and 40 wt. %. In one example, the second mixture includes 30 wt. % of the bioactive glass.

In an example, the second mixture can include a peroxide. The peroxide can be added to the second mixture to catalyst the self-polymerizing composition when the first mixture and the second mixture react. In an example, the peroxide can be chosen from benzoyl peroxide, cumyl peroxide, and cumyl hydroperoxide. In an example, the peroxide is benzoyl peroxide. The second mixture can include the peroxide within a range of about 0.5 wt. % to about 6 wt. %, the weight percent based on the total weight of the second mixture. For example, the second mixture can include the peroxide within a range of from 1 wt. % to 5 wt. %, such as 2 wt. %, 3 wt. %, and 4 wt. %.

The second mixture can also include the diluent. The diluent can be selected from the diluents listed for the first mixture. In one example, the diluent in the second mixture can be TEGDMA. In an example, the second mixture can include the diluent within a range of from about 15 wt. % to about 57 wt. %, the weight percent based on the total weight of the first mixture. For example, the first mixture can include 20 wt. %, 25 wt. %, 30 wt. %, 35 wt. %, 40 wt. %, 45 wt. %, and 50 wt. % of the diluent. In one example, the first mixture comprises 37 wt. % of the cross-linking agent.

In an example, the coating composition of the present disclosure can also be used to deliver therapeutic agents for improving osseointegration and early stage stability of a dental implant under compromised healing conditions. For example, the therapeutic agents can include antibiotics, growth factors, and cytokines, among others.

Figure 1:
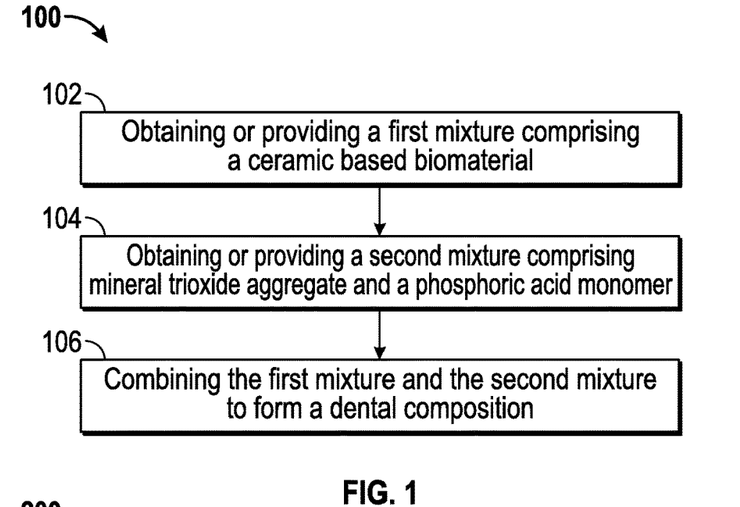
FIG. 1 is a flow diagram of a method for forming a dental implant coating composition.

FIG. 1 illustrates an example method 100 of forming the dental composition. At 102, the method 100 can include obtaining or providing a first mixture including a ceramic based biomaterial. For example, the first mixture can include the HA within a range of about 50 wt. % to about 90 wt. %, the weight percent based on the total weight of the first mixture. At 104, the method 100 can include obtaining or providing a second mixture comprising mineral trioxide aggregate (MTA) and a phosphoric acid monomer. For example, the second mixture can include the phosphoric acid monomer within a range of about 1 wt. % to about 15 wt. %, the weight percent based on the total weight of the second mixture.

Figure 2:
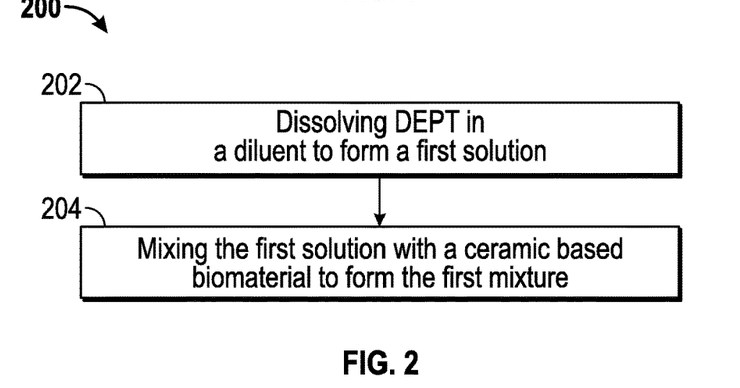
FIG. 2 is a flow diagram of an example method for forming a first mixture of the dental implant coating composition.

As discussed herein, the first mixture can include, along with the ceramic based biomaterial, a diluent and DEPT. In an example, the method 100 can include combining the ceramic based biomaterial, the diluent and DEPT to form the first mixture. FIG. 2 illustrates an example method 200 of obtaining or providing the first mixture comprising a ceramic based biomaterial. At 202, the method 200 can include dissolving the DEPT in the diluent to form a first solution. At 204, the method 200 can include mixing the first solution with the ceramic based biomaterial to form the first mixture. As discussed herein, the first mixture can include about 50 wt. % to about 90 wt. % of the ceramic based biomaterial (e.g., HA), about 15 wt. % to about 55 wt. % of the diluent, and about 2 wt. % to about 8 wt. % of the DEPT, where the weight percent is based on the total weight of the first mixture.

Figure 3:
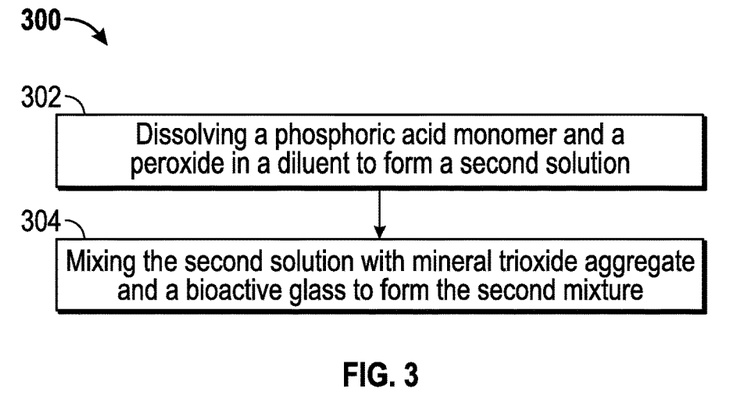
FIG. 3 is a flow diagram of an example method for forming a second mixture of the dental implant coating composition.

As discussed herein, the second mixture can include, along with the MTA and the phosphoric acid monomer, a bioactive glass, a diluent, and a peroxide. For example, the method 100 can include combining the MTA and MDP with the bioactive glass, the diluent, and the peroxide. FIG. 3 illustrates an example method 300 of obtaining or providing the second mixture comprising the MTA and the phosphoric acid monomer. At 302, the method 300 can include dissolving the MDP and the peroxide in the diluent to form a second solution. At 304, the method 300 can include mixing the second solution with the MTA and the bioactive glass to form the second mixture. As discussed herein, the second mixture can include about 5 wt. % to about 50 wt. % of the MTA, about 1 wt. % to about 15 wt. % of the phosphoric acid monomer, about 15 wt. % to about 57 wt. % of the diluent, about 10 wt. % to about 50 wt. % of the bioactive glass, and about 0.5 wt. % to about 6 wt. % of the peroxide, where the weight percent is based on a total weight of the second mixture.

Referring back to FIG. 1, at 106, the method 100 can include combining the first mixture and the second mixture to form the dental composition. In an example, the first and second mixture can be combined together manually or in a dual syringe having a first compartment (e.g., a syringe) including the first mixture and a second compartment (e.g., a syringe) including the second mixture. The dual syringe can include or be coupled to a mixing tip such that when the syringe is activated (e.g., by a user), the first mixture and the second mixture will be combined prior to exiting the mixing tip.

Method 100 can include applying the dental composition to a dental implant. For example, a dental implant configured to be inserted into a dental bone cavity. In an example, applying the dental composition to the dental implant can include coating a portion of an exterior surface of the dental implant, where the portion is configured to be inserted into an implant site within a patient.

Figure 4:
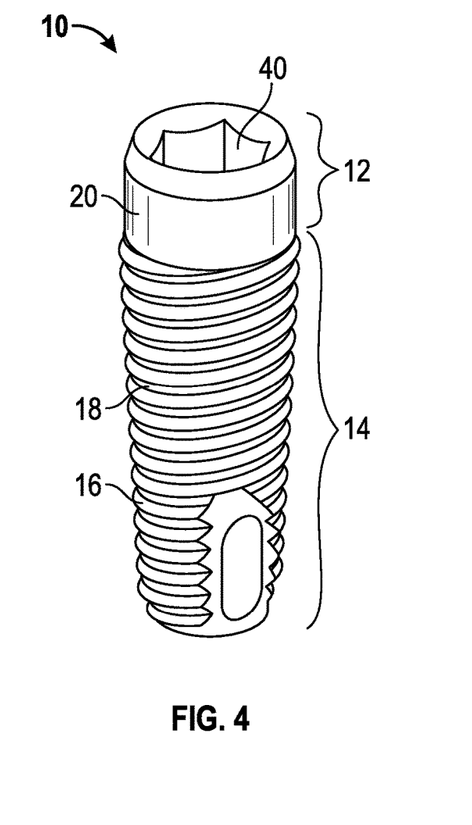
FIG. 4 is a perspective view of an example of a dental implant that can be used with the dental implant coating composition.
Figure 5:
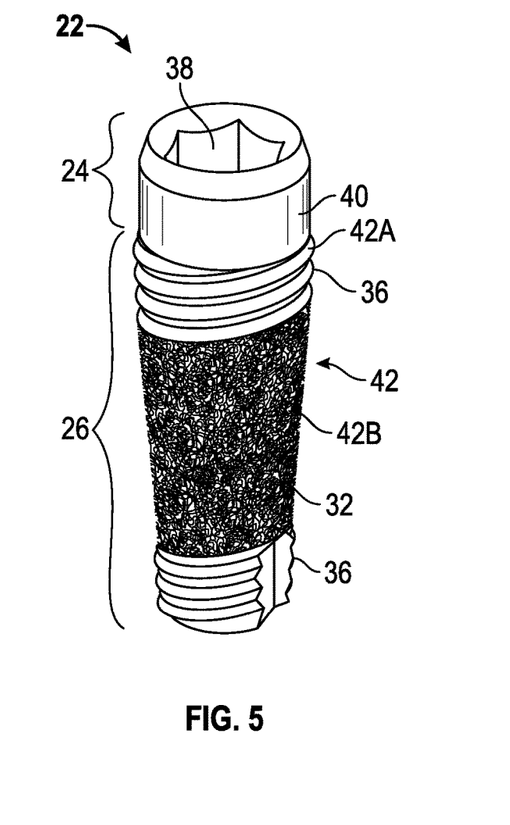
FIG. 5 is a perspective view of an example of a dental implant that can be used with the dental implant coating composition.

In an example, method 100 can include applying the dental composition to an abutment FIGS. 4 and 5 illustrate perspective views of examples of a dental implant that can be used with the dental composition. For example, FIG. 4 illustrates a perspective view of an example of dental implant 10 that be used with the dental composition described herein. The dental implant 10 can be combined with an abutment and provide an anchor for a prosthetic tooth (e.g., a crown) at an edentulous site in a patient's dentition, where a natural tooth has been lost, damaged, or removed. The dental implant 10 can include a recess 40 that can be configured to make with the abutment. For example, the recess 40 can include a polygonal inner surface including a plurality of generally flat surfaces configured to mate with a base of the abutment. In an example, the abutment can be a separate component from the abutment. In another example, the abutment can be integral with the dental implant 10.

The dental implant 10 can be fitted into a dental cavity formed in a patient's dental bone. The dental implant 10 can include a collar portion 12 and a body portion 14. The collar portion 12 can be the portion of the dental implant 10 forming the recess 40 in which the abutment can be inserted. The collar portion 12 can have an exterior surface 20 that can be threaded, partially threaded, or non-threaded, the latter of which is illustrated in FIG. 4. For example, the body portion 14 can include a plurality of threads 16.

The dental implant 10 can include a longitudinally extending body portion 14 adapted to be implanted into the dental cavity formed in the dental bone of a patient. The dental cavity can be formed according to known surgical techniques, for example, by a surgeon drilling into a patient's jaw bone at an edentulous site. The body portion 14 of the dental implant 10 can include an exterior surface 18 for interacting with bone and other tissue, thereby securing the dental implant 10 to the dental bone through osseointegration or other biological or mechanical interactions. The body portion 14 can be made of a biocompatible metal, for example, titanium.

The body portion 14 can be cylindrical, partially cylindrical, or tapered in shape. The exterior surface 18 of the dental implant 21 can be threaded, partially threaded, or non-threaded. As illustrated in the example of FIG. 4, the exterior surface 18 include threads 44 along a length of the body portion 14. As discussed herein, the dental composition can be applied to the exterior surface 18 of the body portion 14 and the exterior surface 20 of the collar portion 12 prior to inserting the dental implant 10 into the dental cavity. The dental composition can form a stabilizing layer between the dental implant 10 and the surrounding dental bone and tissue. In an example, a portion of the exterior surface 18 of the body portion 14 and the exterior surface 20 of the collar portion 12 can include a ceramic based biomaterial. For example, the ceramic based biomaterial can include calcium phosphates, strontium phosphates, calcium carbonates, calcium sulfate, and calcium hydroxide. In an example, the ceramic based biomaterial can be hydroxyapatite.

FIG. 5 illustrates a perspective view of dental implant 22 that can be used with the dental implant coating composition described herein. The dental implant 22 can include a collar portion 24 and a body portion 26. The dental implant 22 can be similar to dental implant 10 (as shown in FIG. 4), except the body portion 26 of the dental implant 22 includes a porous portion 32. The collar portion 24 can form the recess 38 in which an abutment can be inserted. The collar portion 12 can have an exterior surface 40 that can be threaded or non-threaded. As illustrated in the example of FIG. 5, the body portion 26 can include a threaded portion 36 and a porous portion 32. In an example, the threaded portion 36 can be positioned on each side of the porous portion 32. As discussed herein, the dental implant coating composition can be applied to the exterior surface 42 of the body portion 14 and the exterior surface 40 of the collar portion 24. The exterior surface 42 of the body portion 26 can includes threads 42A of the threaded portion 36 and pores 42B of the porous portion 32. The dental composition can be applied to the exterior surfaces 40 and 42 prior to inserting the dental implant 22 into the dental cavity. The dental implant coating composition can form a stabilizing layer between the dental implant 22 and the surrounding dental bone and tissue. In an example, the dental implant 22 can define a central bore that is in communication with the exterior surface 42 via the pores of the porous portion 32. Thus, the dental implant 22 can be inserted into the dental cavity and the dental composition can be inserted into the central bore and move to the exterior surface 42 via the porous portion 32. For example, the dental composition can flow from the central bore to the dental cavity via the porous portion 32 and form a stabilizing layer between the dental implant 22 and the surrounding dental bone and tissue. In an example, the dental composition can infiltrate one or more pores of the porous portion 32 to enhance mechanical strength of the porous portion 32 and to act as a medium for in-growth of dental bone around and into the dental implant 22.

In an example, a portion of at least one of the exterior surfaces 40 and 42 can include a ceramic based biomaterial. That is, the dental implant 22 can be manufactured with the ceramic based biomaterial and the dental composition can be applied to the exterior surfaces 40 and 42 including the ceramic based biomaterial. For example, the ceramic based biomaterial can include calcium phosphates, strontium phosphates, calcium carbonates, calcium sulfate, and calcium hydroxide. In an example, the ceramic based biomaterial can be hydroxyapatite. The above Detailed Description includes references to the accompanying drawings, which form a part of the Detailed Description. The drawings show, by way of illustration, specific embodiments in which the present dental implant can be practiced. These embodiments are also referred to herein as "examples."

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "about" and "approximately" are used to refer to an amount that is nearly, almost, or in the vicinity of being equal to a stated amount. In this document, the term "patient" is intended to include mammals, such as for human documents or veterinary documents.

In the appended claims, the terms "including" and "in which" are used as the plain-English equivalents of the respective terms "comprising" and "wherein." Also, in the following claims, the terms "including" and "comprising" are open-ended, that is, an implant, assembly, kit, or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" should be interpreted to include not just 0.1% to 5%, inclusive, but also the individual values (e.g., 1%, 2%, 3%, and 4%) and the sub-ranges (e.g., 0.1% to 0.5%, 1.1% to 2.2%, 3.3% to 4.4%) within the indicated range.

The Abstract is provided to allow the reader to quickly ascertain the nature of the technical disclosure. It is submitted with the understanding that it will not be used to interpret or limit the scope or meaning of the claims.

What is claimed is:

1. A dental composition for a dental implant insertable into an implant site, comprising:
  a reaction product of a reaction mixture comprising:
    a first mixture comprising:
      a ceramic based biomaterial including hydroxyapatite, a diluent comprising a cross-linking agent, and
a first initiator, and
a second mixture comprising:
mineral trioxide aggregate reacts with moisture at the implant site to form a solid scaffold on the dental implant,
a phosphoric acid monomer reacts with the ceramic based biomaterial and the mineral trioxide aggregate to bond the ceramic based biomaterial to the solid scaffold of mineral trioxide aggregate, and
a second initiator;
wherein the diluent reacts with the phosphoric acid monomer to crosslink at least the phosphoric acid monomer.

2. The dental composition of claim 1, wherein the ceramic based biomaterial further includes one or more of calcium phosphates, strontium phosphates, calcium carbonates, calcium sulfate, and calcium hydroxide.

3. The dental composition of claim 1, wherein about 50 weight percent to about 80 weight percent of the first mixture comprises the ceramic based biomaterial, the weight percent based on a total weight of the first mixture.

4. The dental composition of claim 1, wherein 60 weight percent of the first mixture comprises the ceramic based biomaterial, the weight percent based on a total weight of the first mixture.

5. The dental composition of claim 1, wherein about 5 weight percent to about 50 weight percent of the second mixture comprises the mineral trioxide aggregate, the weight percent based on a total weight of the second mixture.

6. The dental composition of claim 1, wherein the phosphoric acid monomer is chosen from at least one of 1-methacryloyloxydecane-10-phosphate, 1-methacryloyloxyhexane-6-phosphate, 1-methacryloylaminodecane-10-phosphate, 1-acryloylaminohexane-6-phosphate, 1,3-dimethacryloyloxypropane-2-phosphate, and 1,3-dimethacryloylaminopropane-2-phosphate.

7. The dental composition of claim 1, wherein about 1 weight percent to about 15 weight percent of the second mixture comprises the phosphoric acid monomer, the weight percent based on a total weight of the second mixture.

8. The dental composition of claim 1, wherein the first mixture comprises about 15 weight percent to about 55 weight percent of the diluent, the weight percent based on a total weight of the first mixture.

9. The dental composition of claim 1, wherein the first mixture comprises about 2 weight percent to about 8 weight percent of N,N-di(2-hydroxyethyl)-p-toluidine as the first initiator, the weight percent based on a total weight of the first mixture.

10. The dental composition of claim 1, wherein the second mixture further comprises about 10 weight percent to about 50 weight percent of a bioactive glass, the weight percent based on a total weight of the second mixture.

11. The dental composition of claim 1, wherein the second initiator includes a peroxide comprising about 0.5 weight percent to about 6 weight percent of the second mixture, the weight percent based on a total weight of the second mixture.

12. The dental composition of claim 1, wherein the first mixture comprises:
60 weight percent of hydroxyapatite;
35 weight percent of the diluent; and
5 weight percent of the first initiator, wherein the first initiator comprises N,N-di(2-hydroxyethyl)p-toluidine, the weight percent based on a total weight of the first mixture.

13. The dental composition of claim 12, wherein the diluent is tetra-ethylene glycol dimethacrylate.

14. The dental composition of claim 1, wherein the second mixture comprises:
25 weight percent of the mineral trioxide aggregate;
5 weight percent of the phosphoric acid monomer;
3 weight percent of the second initiator, wherein the second initiator comprises a peroxide;
and further comprises 37 weight percent of a diluent and 30 weight percent of a bioactive glass, the weight percent based on a total weight of the second mixture.

15. The dental composition of claim 14, wherein the diluent of a second mixture is tetra-ethylene glycol dimethacrylate, the peroxide is benzoyl peroxide, and the bioactive glass has a formulation of 46.1 mole percent of silicon dioxide, 2.6 mole percent of phosphorus pentoxide, 26.9 mole percent of calcium oxide, and 24.4 mole percent of sodium oxide.

16. A method, comprising:
obtaining or providing the first mixture of claim 1;
obtaining or providing the second mixture of claim 1; and
combining the first mixture and the section mixture to form the reaction product of claim 1.

17. The method of claim 16, wherein obtaining or providing the first mixture comprises: combining the ceramic based biomaterial with the diluent and N,N-di(2-hydroxyethyl)-p-toluidine as the first initiator.

18. The method of claim 17, wherein obtaining or providing the first mixture comprises:
dissolving the N,N-di(2-hydroxyethyl)-p-toluidine in the diluent to form a first solution; and
mixing the first solution with the ceramic based biomaterial to form the first mixture.

19. The method of claim 18, wherein the diluent of the first mixture is a first diluent, and wherein obtaining or providing the second mixture comprises: combining the mineral trioxide aggregate and the phosphoric acid monomer with a second diluent, and a peroxide as the second initiator and further combining with a bioactive glass.

20. The method of claim 16, wherein obtaining or providing the second mixture comprises:
dissolving the phosphoric acid monomer and the peroxide in the diluent to form a second solution; and
mixing the second solution with the mineral trioxide aggregate and further mixing with a bioactive glass to form the second mixture.

* * * * *

UNITED STATES PATENT AND TRADEMARK OFFICE
CERTIFICATE OF CORRECTION

PATENT NO. : 10,478,384 B2
APPLICATION NO. : 14/101936
DATED : November 19, 2019
INVENTOR(S) : Lee et al.

Page 1 of 1

It is certified that error appears in the above-identified patent and that said Letters Patent is hereby corrected as shown below:

In the Claims

In Column 13, Line 2, in Claim 1, delete "initiator," and insert --initiator;-- therefor In Column 14, Line 23, in Claim 15, delete "a" and insert --the-- therefor Signed and Sealed this
Twenty-third Day of March, 2021

Drew Hirshfeld
*Performing the Functions and Duties of the*
*Under Secretary of Commerce for Intellectual Property and*
*Director of the United States Patent and Trademark Office*